United States Patent
Kusumura

(10) Patent No.: US 10,740,677 B2
(45) Date of Patent: Aug. 11, 2020

(54) FEATURE ENUMERATION SYSTEM, FEATURE ENUMERATION METHOD AND FEATURE ENUMERATION PROGRAM

(71) Applicant: NEC Corporation, Tokyo (JP)

(72) Inventor: Yukitaka Kusumura, Tokyo (JP)

(73) Assignee: NEC Corporation, Tokyo (JP)

( * ) Notice: Subject to any disclaimer, the term of this patent is extended or adjusted under 35 U.S.C. 154(b) by 709 days.

(21) Appl. No.: 15/316,075

(22) PCT Filed: Feb. 13, 2015

(86) PCT No.: PCT/JP2015/000682
§ 371 (c)(1),
(2) Date: Dec. 2, 2016

(87) PCT Pub. No.: WO2015/186278
PCT Pub. Date: Dec. 10, 2015

(65) Prior Publication Data
US 2017/0109629 A1 Apr. 20, 2017

(30) Foreign Application Priority Data

Jun. 3, 2014 (JP) .................................. 2014-114923

(51) Int. Cl.
*G06N 3/00* (2006.01)
*G06N 3/12* (2006.01)
(Continued)

(52) U.S. Cl.
CPC ............. *G06N 3/126* (2013.01); *G06F 16/00* (2019.01); *G06N 5/025* (2013.01); *G06N 20/00* (2019.01); *G16B 40/00* (2019.02)

(58) Field of Classification Search
CPC .................................................. G06N 3/126
See application file for complete search history.

(56) References Cited

U.S. PATENT DOCUMENTS

| 6,438,741 B1 * | 8/2002 | Al-omari ......... G06F 16/24542 707/694 |
| 2003/0220926 A1 * | 11/2003 | Huelsman ................ G06N 5/02 |
| 2013/0085977 A1 * | 4/2013 | Junker ................... G06N 5/025 706/47 |

OTHER PUBLICATIONS

L. Zhao et al., "Blosom: A Framework for Mining Arbitrary Boolean Expressions", KDD '06 Proceedings of the 12th ACM SIGKDD International Conference on Knowledge Discovery and Data Mining, pp. 827-832, 2006.
(Continued)

*Primary Examiner* — Hien D Khuu
(74) *Attorney, Agent, or Firm* — Finnegan, Henderson, Farabow, Garrett & Dunner, L.L.P.

(57) ABSTRACT

An enumeration plan generation unit 81 generates a set of logical formula structures each representing a way of combining logical formula expressions each representing a combination of features by use of the features of learning data items and the maximum number of features to be combined, and generates partial logical formula structures by dividing a logical formula expression included in each of the generated logical formula structures into two, and generates an enumeration plan in which the partial logical formula structures are linked to the logical formula structure from which the partial logical formula structures are divided. The feature generation unit 82 generates a new feature that is a combination of the features corresponding to the generated partial logical formula structures. Furthermore, the enumeration plan generation unit 81 divides the logical formula structure into two such that the numbers of the features included in the two partial logical formula structures generated from each of the logical formula structures are substantially equal.

16 Claims, 10 Drawing Sheets

(51) Int. Cl.
*G06N 20/00* (2019.01)
*G06N 5/02* (2006.01)
*G06F 16/00* (2019.01)
*G16B 40/00* (2019.01)

(56) References Cited

OTHER PUBLICATIONS

R. Vimieiro et al., "Mining disjunctive minimal generators with TitanicOR", Expert Systems with Applications, vol. 39, Issue 9, pp. 8228-8238, 2012.
G. Li et al., "Sampling Minimal Frequent Boolean (DNF) Patterns", KDD '12 Proceedings of the 18$^{th}$ ACM SIGKDD International Conference on Knowledge Discovery and Data Mining, pp. 87-95, 2012.
S. Perkins et al., "Online Feature Selection using Grafting", Proceedings of the Twentieth International Conference on Machine Learning (ICML-2003), 2003.
K. Sadohara, "Feature selection using Boolean kernels for the learning of Boolean functions", in IPSJ SIG Technical Reports, vol. 2004, No. 29, (2004-ICS-135 (33)), pp. 187-192, Mar. 2004.
K. Makino, "Logical Analysis of Data and Boolean Functions", Proceedings of the 1998 IEICE General Conference, vol. 1, No. TD-1-3, pp. 476-477, Mar. 1998.
International Search Report and Written Opinion of ISA dated May 19, 2015, in corresponding PCT International Application.

\* cited by examiner

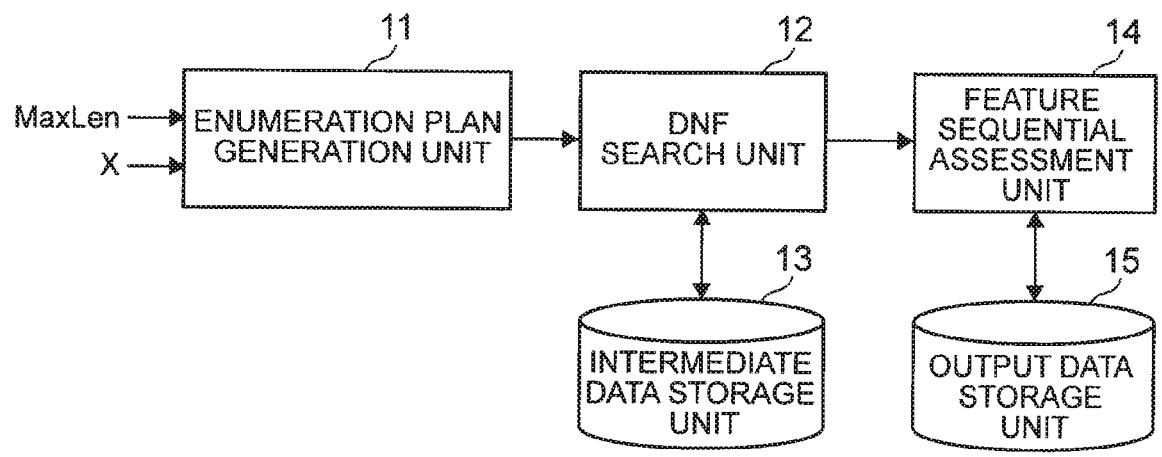

FIG. 5
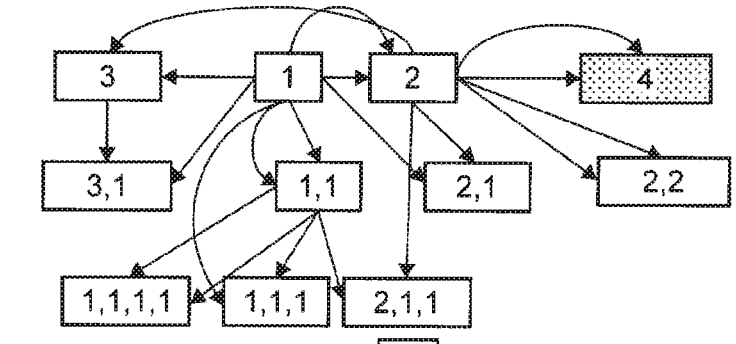
(a)
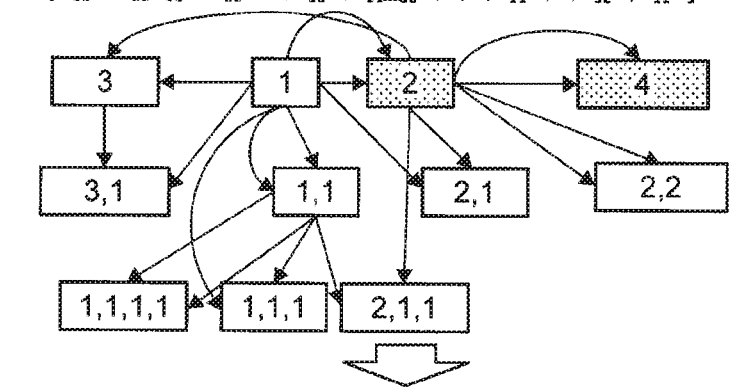
(b)
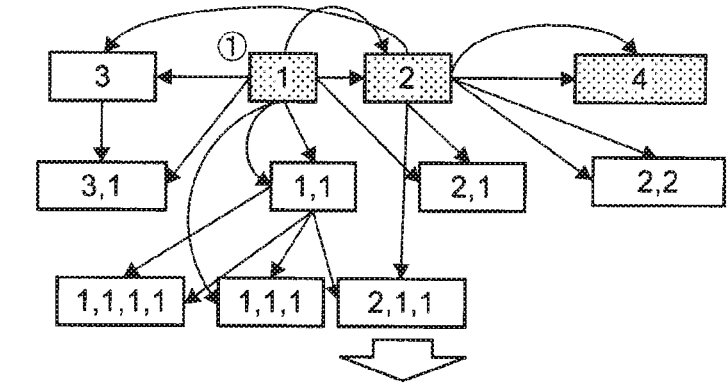
(c)
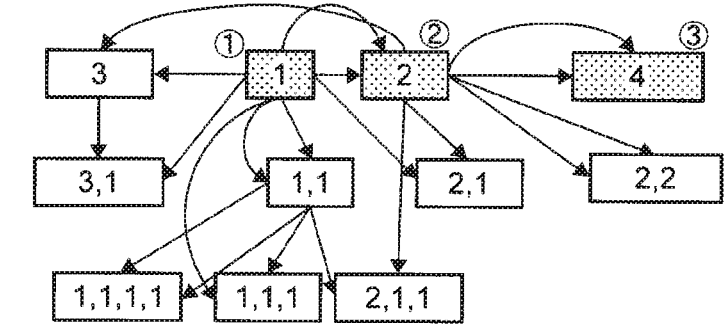
(d)

| DNFLabel | cacheFlag | P1 | P2 |
|---|---|---|---|
| 1 | | None | None |
| 2 | | 1 | 1 |
| 4 | | 2 | 2 |
| 3 | | 1 | 2 |
| 3,1 | | 1 | 3 |
| 2,2 | | 2 | 2 |
| 1,1 | | 1 | 1 |
| 1,1,1,1 | | 1,1 | 1,1 |
| 1,1,1 | | 1 | 1,1 |
| 2,1,1 | | 1,1 | 2 |
| 2,1 | | 1 | 2 |

TRUE/FALSE

| DNFLabel | cacheFlag | P1 | P2 | CALCULATION COST | MEMORY COST |
|---|---|---|---|---|---|
| 1 | | None | None | 8 | 1 |
| 2 | | 1 | 1 | 7 | 2 |
| 4 | | 2 | 2 | 0 | 4 |
| 3 | | 1 | 2 | 1 | 3 |
| 3,1 | | 1 | 3 | 0 | 4 |
| 2,2 | | 2, | 2 | 0 | 4 |
| 1,1 | | 1 | 1 | 4 | 2 |
| 1,1,1,1 | | 1,1 | 1,1 | 0 | 4 |
| 1,1,1 | | 1 | 1,1 | 0 | 3 |
| 2,1,1 | | 1,1 | 2 | 0 | 4 |
| 2,1 | | 1 | 2 | 0 | 3 |

(a)

| DNFLabel | cacheFlag | P1 | P2 | CALCULATION COST | MEMORY COST |
|---|---|---|---|---|---|
| 1 | TRUE | None | None | 8 | 1 |
| 2 | TRUE | 1 | 1 | 7 | 2 |
| 4 | FALSE | 2 | 2 | 0 | 4 |
| 3 | FALSE | 1 | 2 | 1 | 3 |
| 3,1 | FALSE | 1 | 3 | 0 | 4 |
| 2,2 | FALSE | 2, | 2 | 0 | 4 |
| 1,1 | TRUE | 1 | 1 | 4 | 2 |
| 1,1,1,1 | FALSE | 1,1 | 1,1 | 0 | 4 |
| 1,1,1 | FALSE | 1 | 1,1 | 0 | 3 |
| 2,1,1 | FALSE | 1,1 | 2 | 0 | 4 |
| 2,1 | FALSE | 1 | 2 | 0 | 3 |

```
enum (row[i])
 P1_SIZE= getSize(row[i].P1)
 P2_SIZE= getSize(row[i].P2)
 For a=0 to P1_SIZE
 For b=0 to P2_SIZE
  NewDNF = get(row[i],a*P1_SIZE+b)
  Output(NewDNF) #OUTPUT NEW DNF TO FEATURE SEQUENTIAL
                          ASSESSMENT UNIT
 IF row[i].cacheFlag
  insert NewDNF to INTERMEDIATE DATA STORAGE UNIT
```

(a)

```
get (row,i)
 IF row.label in INTERMEDIATE DATA STORAGE UNIT
  OUTPUT FEATURE CORRESPONDING TO i-TH DNF
 ELSE #GENERATE ALSO PARENT BECAUSE CORRESPONDING
        FEATURE IS NOT CACHED
 a=getSize(row.P1)
 p1_id=i/a
 p2_id=i-a*p1_id DNF1 = get(row.P1, p1_id) #REFERENCE TO RESULT OF PARENT 1
 DNF2 = get(row.P2, p2_id) #REFERENCE TO RESULT OF PARENT 2

IF IsAND(row) #LABELS CONTAIN ONLY AND TERMS
  NewDNF = AND(DNF1, DNF2) #GENERATE AND COMBINATION
 ELSE
  NewDNF = OR(DNF1, DNF2) #GENERATE OR COMBINATION
```

(b)

FEATURE ENUMERATION SYSTEM, FEATURE ENUMERATION METHOD AND FEATURE ENUMERATION PROGRAM

CROSS-REFERENCE TO RELATED PATENT APPLICATIONS

This application is a National Stage Entry of International Application No. PCT/JP2015/000682, filed Feb. 13, 2015, which claims priority from Japanese Patent Application No. 2014-114923, filed Jun. 3, 2014. The entire contents of the above-referenced applications are expressly incorporated herein by reference.

TECHNICAL FIELD

The present invention relates to a feature enumeration system, a feature enumeration method, and a feature enumeration program that enumerate a new feature that is a combination of the features of learning data items.

BACKGROUND ART

Data mining is a technique for finding useful knowledge previously unknown from a large amount of information. To efficiently conduct data mining, a process for generating a new feature by processing the features used for the data mining.

As a method for generating a new feature, is known a method in which each feature is represented as a two-valued feature, and the two-valued features are combined with AND/OR operators, which generates a logical formula as a new feature.

For example, to represent each day of the week, the days can be represented as seven types of two-valued features (IS_Sunday, IS_Monday, IS_Tuesday, IS_Wednesday, IS_Thursday, IS_Friday, and IS_Saturday). Similarly, to represent a day with ante meridiem or post meridiem, a day can be represented as two types of two-valued features (IS_a.m., and IS_p.m.).

Based on the two-valued features, a new feature "weekend post meridiem" can be generated. Specifically, a logical formula that is a combination of the two-valued features with AND/OR operators "(IS_Saturday AND IS_p.m.) OR (IS_Sunday AND IS_p.m.)" represents a feature "weekend post meridiem".

In order to solve an actual problem, it is often necessary to generate a new feature by appropriately combining features as described above. It is, however, not so easy to find an appropriate way of combining features. For example, when original data includes 100 features and five features of the 100 features are combined with AND/OR operators, there are logical formulae of combinations on the order of $100^5 \times 2^4$ (in other words, 160 billion). Thus, simply combining the two-valued features wastes a large amount of memory and an immense amount of time for calculation.

NPL 1 and NPL 2 describe methods for enumerating features. In the methods described in NPL 1 and NPL 2, the features that are combinations of features with AND operators (Disjunctive normal form (DNF)) are enumerated, and then the enumerated features are combined with OR operators, which generates a new feature.

NPL 3 describes a method for extracting the patterns in DNF frequently used. NPL 4 describes an exemplary method for assessing features.

CITATION LIST

Non Patent Literature

NPL 1: Lizhuang Zhao, Mohammed J. Zaki, Naren Ramakrishnan, "BLOSOM: A Framework for Mining Arbitrary Boolean Expressions", KDD '06 Proceedings of the 12th ACM SIGKDD international conference on Knowledge discovery and data mining, p. 827-832, 2006

NPL 2: Vimieiro Renato, Moscato Pablo, "Mining disjunctive minimal generators with TitanicOR", Expert Systems with Applications Vol. 39, Issue 9, p. 8228-8238, 2012

NPL 3: Geng Li, Mohammed J. Zaki, "Sampling Minimal Frequent Boolean (DNF) Patterns", KDD '12 Proceedings of the 18th ACM SIGKDD international conference on Knowledge discovery and data mining, p. 87-95, 2012

NPL 4: S. Perkins, J. Theiler, "Online Feature Selection using Grafting", In ICML, 2003

SUMMARY OF INVENTION

Technical Problem

In the methods described in NPL 1 and NPL 2, however, an enumeration method in which only the features combined with AND operators are initially enumerated, and then the features are combined with OR operators one by one is used to enumerate DNF. These methods require a large memory space. For example, on the assumption that a feature of a combination of five features with AND/OR operators is enumerated from 100 original features with the method of NPL 1, there are $100^4$ possible combinations of features each of which is a combination of four features with AND/OR operators. All of the possible features need to be stored in the memory. This requires a large memory space.

On the other hand, in order to prevent the requirement of a large memory space, a method in which, instead of caching a new feature in the memory when the feature is generated, a new feature is calculated each time may be considered. In this method, however, it is necessary to regenerate all of the combinations from the beginning. This requires an immense amount of time for the calculation, and thus prevents the features from being enumerated at high speed.

Alternatively, in order to prevent waste of a large space of the memory and an immense amount of time for calculation, random sampling of the features using the method described in NPL 3 can be considered. However, the combinations extracted by the method described in NPL 3 do not have completeness. Thus, it is difficult in the method to generate a better feature.

In light of the foregoing, an objective of the present invention is to provide a feature enumeration system, a feature enumeration method, and a feature enumeration program that can enumerate a new feature at high speed while allowing the features to have completeness and preventing waste of the memory.

Solution to Problem

A feature enumeration system according to the present invention includes: an enumeration plan generation unit that generates a set of logical formula structures each representing a way of combining logical formula expressions each representing a combination of features by use of features of learning data items and a maximum number of features to be combined, generates partial logical formula structures by dividing a logical formula expression included in each of the generated logical formula structures into two, and generates an enumeration plan in which the partial logical formula structures are linked to the logical formula structure from which the partial logical formula structures are divided; and a feature generation unit that generates a new feature that is a combination of the features corresponding the generated partial logical formula structure, wherein the enumeration plan generation unit divides the logical formula structure into two such that numbers of the features included in the two partial logical formula structures generated from each of the logical formula structures are substantially equal.

Another feature enumeration system according to the present invention includes an enumeration plan generation unit and a feature generation unit. The enumeration plan generation unit generates a set of logical formula structures each representing a way of combining logical formula expressions each representing a combination of features by use of the features of learning data items and the maximum number of features to be combined, and generates an enumeration plan in which the relationship between the logical formula structure and the generated partial logical formula structures each representing a part of the logical formula structure is represented as a graph structure; and the feature generation unit that generates a new feature that is a combination of the features in accordance with the partial logical formula structures, wherein the enumeration plan generation unit selects the partial logical formula structures from the enumeration plan such that the size of a space necessary to store the new feature generated by the feature generation unit can be reduced and more parts of the logical formula structure can be represented.

A feature enumeration method according to the present invention includes: generating a set of logical formula structures each representing a way of combining logical formula expressions each representing a combination of features by use of features of learning data items and a maximum number of features to be combined; generating partial logical formula structures by dividing a logical formula expression included in each of the generated logical formula structures into two, and generating an enumeration plan in which the partial logical formula structures are linked to the logical formula structure from which the partial logical formula structures are divided; and generating a new feature that is a combination of the features corresponding to the generated partial logical formula structures, wherein, when the enumeration plan is generated, the logical formula structure is divided into two such that numbers of the features included in the two partial logical formula structures generated from each of the logical formula structures are substantially equal.

Another feature enumeration method according to the present invention includes: generating a set of logical formula structures each representing a way of combining logical formula expressions each representing a combination of features by use of features of learning data items and a maximum number of features to be combined; generating an enumeration plan in which a relationship between the logical formula structure and the generated partial logical formula structures each representing a part of the logical formula structure is represented as a graph structure; selecting the partial logical formula structures from the enumeration plan such that a size of a space necessary to store the new feature generated in accordance with the partial logical formula structures is able to be reduced and more parts of the logical formula structure are able to be represented; and generating a new feature that is a combination of the features corresponding to the partial logical formula structures.

A feature enumeration program according to the present invention for causing a computer to execute: an enumeration plan generation process of generating a set of logical formula structures each representing a way of combining logical formula expressions each representing a combination of features by use of features of learning data items and a maximum number of features to be combined, and generating the partial logical formula structures by dividing a logical formula expression included in each of the generated logical formula structures into two and linking the partial logical formula to the logical formula structure from which the partial logical formula structures are divided, to generate an enumeration plan; and a feature generation process of generating a new feature that is a combination of the features corresponding to the generated partial logical formula structures, wherein the logical formula structure is divided into two in the enumeration plan generation process such that numbers of the features included in the two partial logical formula structures generated from each of the logical formula structures are substantially equal.

A feature enumeration program according to the present invention for causing a computer to execute: an enumeration plan generation process of generating a set of logical formula structures each representing a way of combining logical formula expressions each representing a combination of features by use of features of learning data items and a maximum number of features to be combined, and generating an enumeration plan in which a relationship between the logical formula structure and the generated partial logical formula structures each representing a part of the logical formula structure is represented as a graph structure; and a feature generation process of generating a new feature that is a combination of the features corresponding to the partial logical formula structures, wherein the partial logical formula structures are selected from the enumeration plan in the enumeration plan generation process such that a size of a space necessary to store the new feature generated in the feature generation process is able to be reduced and more parts of the logical formula structure are able to be represented.

ADVANTAGEOUS EFFECTS OF INVENTION

According to the present invention, a new feature can be enumerated at high speed while the features are allowed to have completeness and waste of the memory is prevented. In other words, using the technical means described in the "Solution to Problem" to solve the technical problem described in the "Technical Problem" can provide the technical efforts described in this "Advantageous Effects of Invention".

BRIEF DESCRIPTION OF DRAWINGS

FIG. 1 It depicts a block diagram illustrating an exemplary embodiment of a feature enumeration system according to the present invention.

FIG. 2 It depicts an explanatory diagram illustrating exemplary features of learning data items.

FIGS. 5(a) to 5(d) They depict explanatory diagrams illustrating an exemplary operation of a topological sort.

FIGS. 11(a) and 11(b) They depict explanatory diagrams illustrating specific examples of processes that a DNF search unit 12 performs.

DESCRIPTION OF EMBODIMENTS

Figure 3:
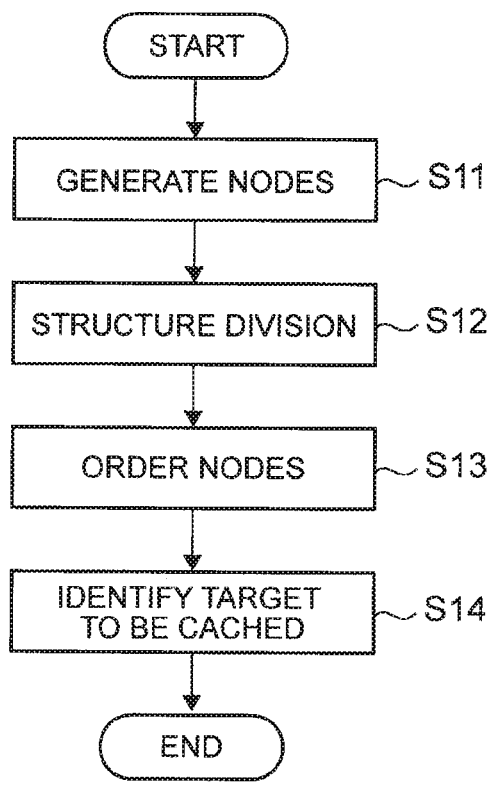
FIG. 3 It depicts a flowchart of an exemplary process that an enumeration plan generation unit 11 performs.

Hereinafter, an exemplary embodiment of the present invention will be described with reference to the appended drawings. FIG. 1 depicts a block diagram illustrating an exemplary embodiment of a feature enumeration system according to the present invention. In the following description, a logical formula representing a combination of two-valued features will be represented as DNF. The DNF is a logical formula represented as $Z= \vee \wedge_i z_i$, and is represented as a formula that is a combination of terms only including logical conjunction with logical disjunction. An arbitrary logical formula can be converted into DNF by equivalent conversion.

An enumeration problem on DNF will be described in the present exemplary embodiment. However, the present invention can similarly be applied to an enumeration problem on Conjunctive normal form (CNF) represented as a formula that is a combination of the terms only including logical disjunction with logical conjunction.

Additionally, in the following description, the number of features included in a logical formula is defined as the length of the logical formula. FIG. 2 depicts an explanatory diagram illustrating exemplary features of learning data items. The table (matrix) illustrated in FIG. 2 as an example represents, as 1/0, whether sample data items $s_1$ to $s_5$ that are the learning data items each have features $f_1$ to $f_5$.

For example, when a logical formula $f_1 \vee f_3$ having a length 2 is calculated for each learning data item, $f_1 \vee f_3 = [1, 1, 1, 1, 0]$ is found. Similarly, for example, when a logical formula $f_1 \wedge f_4$ having the length 2 is calculated for each learning data item, $f_2 \wedge f_4 = [0, 0, 1, 0, 0]$ is found. Furthermore, for example, when a logical formula $(f_2 \wedge f_4) \vee f_5$ having a length 3 is calculated for each learning data item, $(f_2 \wedge f_4) \vee f_5 = [0, 0, 1, 1, 1]$ is found.

The feature enumeration system of the present exemplary embodiment illustrated in FIG. 1 as an example includes an enumeration plan generation unit 11, a DNF search unit 12, an intermediate data storage unit 13, a feature sequential assessment unit 14, and an output data storage unit 15.

To the feature enumeration system of the present exemplary embodiment are input a two-valued matrix X indicating whether the learning data items have designated features, and a maximum number MaxLen of features to be combined. For example, the matrix illustrated in FIG. 2 as an example is input as the two-valued matrix X. The MaxLen is designated, for example, by the user.

When the two-valued matrix X and the MaxLen are input to the enumeration plan generation unit 11, the enumeration plan generation unit 11 generates logical formulae each representing a combination of the features within a length of MaxLen by use of the features of the learning data items and the MaxLen. Furthermore, in the present exemplary embodiment, the enumeration plan generation unit 11 generates a set of the logical formula structures each representing a way of combining the generated logical formulae. In the present exemplary embodiment, the logical formula is represented in DNF. Thus, the logical formula structure is referred to as a DNF label.

A DNF label represents a logical formula as the number of features included in the AND terms and a comma representing an OR operator. For example, a DNF label represented as [3] represents "A and B and C". Similarly, for example, a DNF label represented as [1, 1] represents "A or B". Similarly, for example, a DNF label represented as [1, 3] represents "A or (B and C and D)". Herein, A, B, C, and D represent a feature.

Next, the enumeration plan generation unit 11 divides the logical formula expression included in the generated logical formula structure into two partial logical formula structures. In the present exemplary embodiment, the enumeration plan generation unit 11 represents the relationship between the generated logical formula structure and the partial logical formula structures each representing a part of the generated logical formula structure as a graph structure. Each node in the graph structure is the logical formula structure or the partial logical formula structure. The graph structure represented as described above will be referred to as an enumeration plan hereinafter. Generating such a graph structure links the logical formula structure from which the two partial logical formula structures are divided to the two divided partial logical formula structures. The graph structure is represented, for example, as a directed acyclic graph (DAG).

Hereinafter, a process in which the enumeration plan generation unit 11 generates a graph structure will specifically be described. FIG. 3 depicts a flowchart of an exemplary process that the enumeration plan generation unit 11 performs. First, the enumeration plan generation unit 11 generates all the combinations of DNF labels within a length of MaxLen (step S11 in FIG. 3). For example, when MaxLen=4 holds, DNF labels [4], [3, 1], [3], [2, 2], [2, 1, 1], [2, 1], [2], [1, 1, 1, 1], [1, 1, 1], [1, 1], [1] are generated. The set of the DNF labels generated in this example can be called a set of the logical formula structures each representing a way of combining the logical formula expressions each representing a combination of the features.

Next, the enumeration plan generation unit 11 performs structure division (step S12 in FIG. 3). Specifically, the enumeration plan generation unit 11 identifies a parent node by dividing the generated DNF label, and generates the edges connecting the nodes.

The enumeration plan generation unit 11 identifies a parent node based on the following procedure. When the DNF label to be divided only contains AND terms and the number of the AND terms is N, the enumeration plan generation unit 11 divides the DNF label into a partial DNF label having a length of ceiling (N/2) and a partial DNF label having a length of N-ceiling (N/2). In this example, the ceiling ( ) function is a function to round up the number after the decimal point.

On the other hand, when the DNF label to be divided includes OR terms (in other words, a comma), the enumeration plan generation unit 11 divides the comma-delimited sequence into two partial DNF labels. At that time, the enumeration plan generation unit 11 divides the DNF label so as to minimize the difference between the numbers of features included in the two partial DNF labels. In other words, the enumeration plan generation unit 11 divides each DNF label into two such that the numbers of features included in the two partial DNF labels generated from the DNF label are substantially equal.

Hereinafter, with an example in which a DNF label is represented as [1, 1, 2, 3, 4], an algorithm used to divide the DNF label into a set $S_1$ and a set S2 will be described. The $S_1$ and S2 are initialized into a blank state in an initial state.

First, the enumeration plan generation unit 11 sorts the DNF label in descending order. When the result of the sorting is stored in sorted_list, sorted_list=[4, 3, 2, 1, 1] holds. The enumeration plan generation unit 11 calculates the sum of the numbers included in S1 and the sum of the numbers included in S2 so as to put the first number of the sorted_list in the set of which sum is smaller. Then, the enumeration plan generation unit 11 deletes the put number and the comma following the put number from the sorted_list.

In the initial state of the example, both the sum of the numbers included in S1 and the sum of the numbers included in S2 are equally zero. Thus, the enumeration plan generation unit 11 puts the first number "4" in S1 and deletes the first number "4" from the sorted_list. Thus, sorted_list=[3, 2, 1, 1], S1=[4], and S2=[ ] hold.

At that time, the sum of the numbers included in S1 is four, and the sum of the numbers included in S2 is zero. Accordingly, the enumeration plan generation unit 11 puts the first number "3" in S2 and deletes the first number "3" from the sorted_list. Thus, sorted_list=[2, 1, 1], S1=[4], and S2=[3] hold. Thus, the sum of the numbers included in S1 is four, and the sum of the numbers included in S2 is three. Accordingly, the enumeration plan generation unit 11 puts the first number "2" in S2 and deletes the first number "2" from the sorted_list. Thus, sorted_list=[1, 1], S1=[4], and S2=[3, 2] hold.

After that, similarly, the sum of the numbers included in S1 is four, and the sum of the numbers included in S2 is five. Accordingly, the enumeration plan generation unit 11 puts the first number "2" in S1 and deletes the first number "2" from the sorted_list. Thus, sorted_list=[1], S1=[4, 1], and S2=[3, 2] hold. Finally, the sum of the numbers included in S1 is five, and the sum of the numbers included in S2 is also five. Accordingly, the enumeration plan generation unit 11 puts the first number "1" in S1 and deletes the first number "1" from the sorted_list. Thus, sorted_list=[ ], S1=[4, 1, 1], and S2=[3, 2] hold.

As a result, the DNF label is divided into two partial DNF labels [4, 1, 1], and [3, 2]. Then, the enumeration plan generation unit 11 determines the two partial DNF labels as parent nodes and the DNF label from which the two partial DNF labels are divided as a child node, and generates the edges from the parent nodes to the child node.

Figure 4:
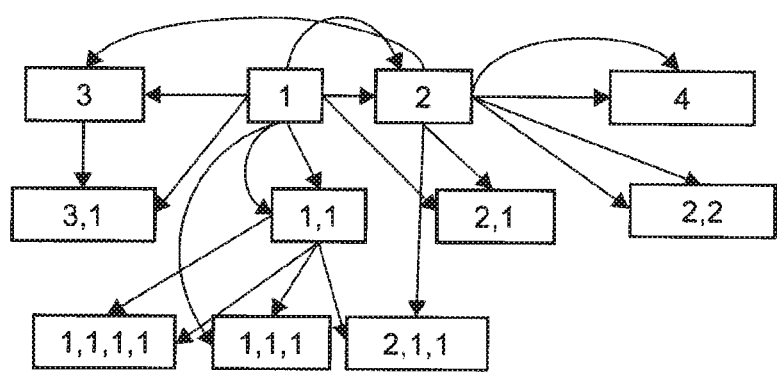
FIG. 4 It depicts an explanatory diagram illustrating an exemplary graph structure.

FIG. 4 depicts an explanatory diagram of an exemplary graph structure. The graph illustrated in FIG. 4 as example is an exemplary DAG when MaxLen=4 holds.

Next, the enumeration plan generation unit 11 orders the nodes (DNF labels) (step S13 in FIG. 3). In the present exemplary embodiment, the enumeration plan generation unit 11 orders the nodes with a topological sort. It is known that DAG can topologically be sorted. A topological sort can order a DAG while maintaining the parent-child relationship (the relationship before and behind an arrow).

Hereinafter, the operation for ordering the nodes of the DAG illustrated in FIG. 4 as an example with a topological sort will be described. FIGS. 5(*a*) to 5(*d*) and FIGS. 6(*e*) to 6(*g*) are explanatory diagrams of exemplary operations of topological sorts. First, the enumeration plan generation unit 11 sorts a set S of DNF labels in descending order. As a result, a DNF label [4] is the first element. Then, the enumeration plan generation unit 11 checks the node of the DNF label [4] as a visited node (FIG. 5(*a*)).

Next, the enumeration plan generation unit 11 follows the output edge of the node of the DNF label [4], and checks the antecedent node of the DNF label [2] as a visited node (FIG. 5(*b*)). Similarly, the enumeration plan generation unit 11 follows the output edge of the node of the DNF label [2], and checks the antecedent node of the DNF label [1] as a visited node. The node of the DNF label [1] does not have a parent node. Thus, the enumeration plan generation unit 11 sets the node of the DNF label [1] as the first node (FIG. 5(*c*)).

At that time, all the parent nodes of the node of the DNF label [2] are ordered. Thus, the enumeration plan generation unit 11 sets the node of the DNF label [2] as the second node. Similarly, all the parent nodes of the node of the DNF label [4] are ordered. Thus, the enumeration plan generation unit 11 sets the node of the DNF label [4] as the third node (FIG. 5(*d*)).

Figure 6:
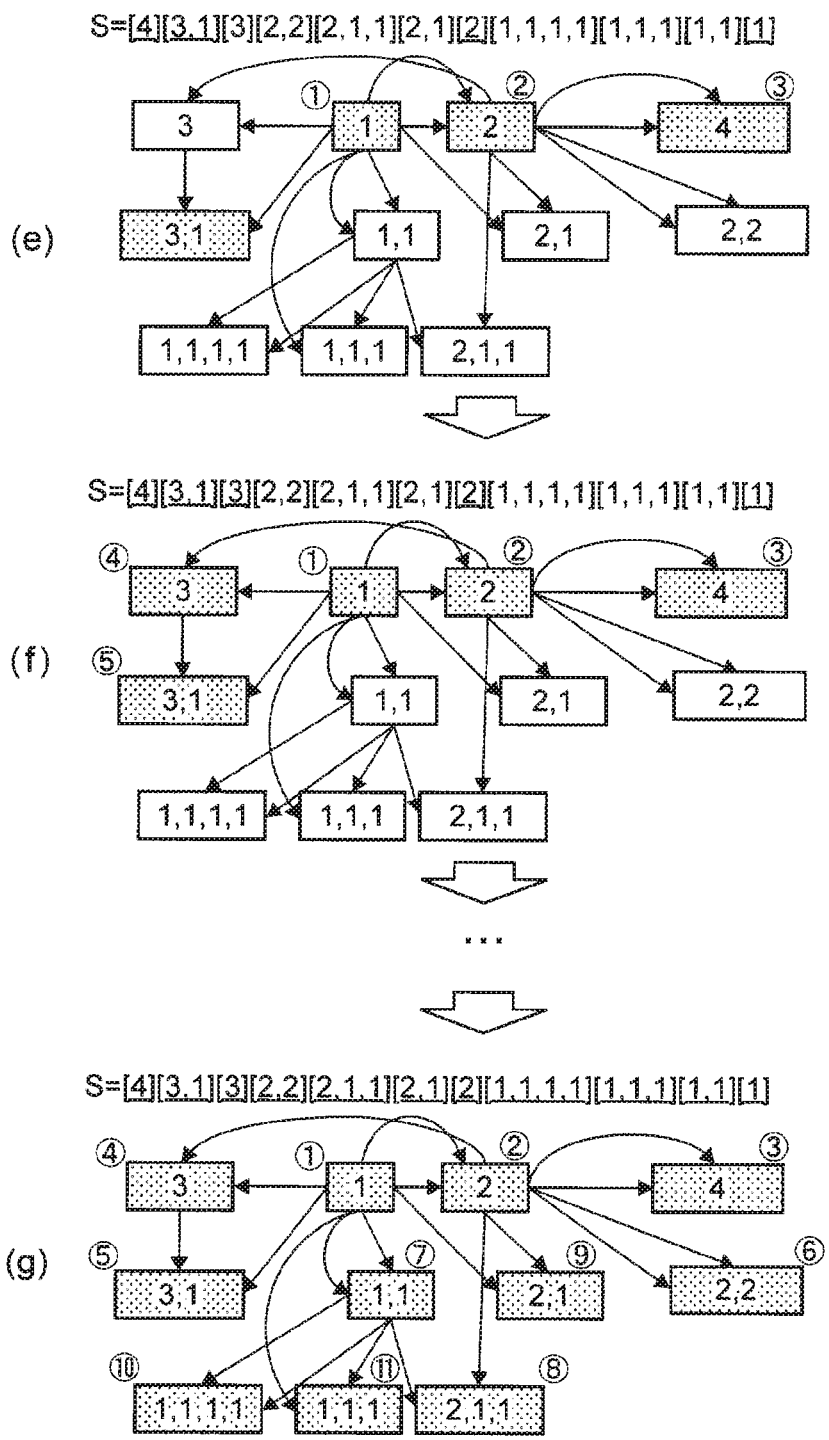
FIGS. 6(e) to 6(g) They depict explanatory diagrams illustrating an exemplary operation of a topological sort.

Next, the enumeration plan generation unit 11 selects the DNF label [3, 1] that is the second element from the top of the set S of DNF labels, and checks the node of the DNF label [3, 1] as a visited node (FIG. 6(*e*)). The enumeration plan generation unit 11 follows the output edge of the node of the DNF label [3, 1], and checks the antecedent node of the DNF label [3] as a visited node.

All the parent nodes of the node of the DNF label [3] are ordered. Thus, the enumeration plan generation unit 11 sets the node of the DNF label [3] as the fourth node. Similarly, all the parent nodes of the node of the DNF label [3, 1] are ordered. Thus, the enumeration plan generation unit 11 sets the node of the DNF label [3, 1] as the fifth node (FIG. 6(*f*)). After that, the enumeration plan generation unit 11 repeats similar operations such that all the nodes are ordered (FIG. 6(*g*)).

Figure 7:
FIG. 7 It depicts an explanatory diagram illustrating an exemplary enumeration plan represented in a tabular form.

The enumeration plan represented as the graph structure can also be represented in a tabular form. FIG. 7 depicts an explanatory diagram illustrating an exemplary enumeration plan represented in a tabular form. In the example illustrated in FIG. 7, the enumeration plan links a DNF label to the two parent DNF labels of the DNF label. Additionally, the enumeration plan can include a flag (cacheFlag) indicating whether the DNF label is to be cached.

Next, the enumeration plan generation unit 11 identifies a target to be cached (step S14 in FIG. 3). Specifically, the enumeration plan generation unit 11 identifies the feature to be stored in the intermediate data storage unit 13. At that time, the enumeration plan generation unit 11 selects the partial DNF labels from the enumeration plan such that such that the size of a space necessary to store a new feature generated based on the logical formula structures (the logical formulae) identified with the DNF labels in the intermediate data storage unit 13 can be reduced and more parts of the logical formula structure can be represented. The fact that more parts of the logical formula structure can be represented means that the reusability of the partial logical formula structures is increased. The new feature is generated by the DNF search unit 12 described below.

In the present exemplary embodiment, the enumeration plan generation unit 11 identifies a target to be cached in accordance with the calculation cost and memory cost. In the present exemplary embodiment, the calculation cost is the number of times of reference to the DNF label in the enumeration plan. Specifically, the calculation cost is the number of times of reference to the DNF label as a parent node. The memory cost is the size of the memory space necessary to store the features, and is simply represented as the sum of the numbers included in the DNF label.

Figure 8:
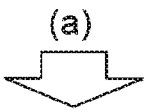
FIGS. 8(a) and 8(b) They depict explanatory diagrams illustrating exemplary calculation costs and memory costs.

FIGS. 8(a) and 8(b) depict an explanatory diagram illustrating an example in which the calculation costs and the memory costs are found in accordance with the enumeration plan illustrated in FIG. 4 as an example. In the example illustrated in FIGS. 8(a) and 8(b), the calculation cost is the number of times of reference to the DNF label in the enumeration plan, and the memory cost is the sum of the numbers included in the DNF label. When a target to be cached is not identified as illustrated in FIG. 8(a), the column of cacheFlag is in a blank state.

The enumeration plan generation unit 11 sorts the nodes referenced as a parent node once or more (in other words, the calculation cost is one or more) in descending order, and identifies the top K nodes as the nodes to be cached. The number of nodes to be selected is equal to or smaller than the number that can be stored in the cache size to which a memory size M for the generated features is designated.

When the original number of features is p and the vector length is n, the cache size of the node set S is found by the following expression 1.

[Mathematical Formula 1]

$$\Sigma^{dnf \in S} 4 \times n \times p^{sum(dnf.label)} \qquad \text{(expression 1)}$$

In the expression 1, the sum(dnf.label) represents the sum of the numbers included in the DNF label. Furthermore, the expression 1 is multiplied by four on the assumption that a variable requires four bytes. For example, when the vector length n=10 and the original number p of features=10 hold, the cache of the DNF label [1] and DNF label [2] is found by the following expression 2.

$$\text{Cashesize}([1],[2])=4*10*10+4*10*10^2=4400 \text{ byte} \qquad \text{(expression 2)}$$

As described in the expression 2, the DNF represented as the DNF label [1] is on the order of p. In other words, the cache size of the DNF label [1] is p×the length 10×four bytes. Meanwhile, the DNF represented as the DNF label [2] is on the order of $p^2$. In other words, the cache size of the DNF label [2] is $p^2$×the length 10×four bytes. The DNF represented as the DNF label [1, 1] is also on the order of $p^2$. Thus, the cache size of the DNF label [1, 1] is the same as the cache size of the DNF represented as the DNF label [2].

In the present exemplary embodiment, it is assumed that the DNF labels [1], [2], and [1, 1] are identified as the DNF labels to be cached. On that assumption, the enumeration plan generation unit 11 puts "TRUE" in the cells of the DNF labels to be cached in the cacheFlag, and puts "FALSE" in the cells of the DNF labels not to be cached in the cacheFlag as illustrated in FIG. 8(b).

Figure 9:
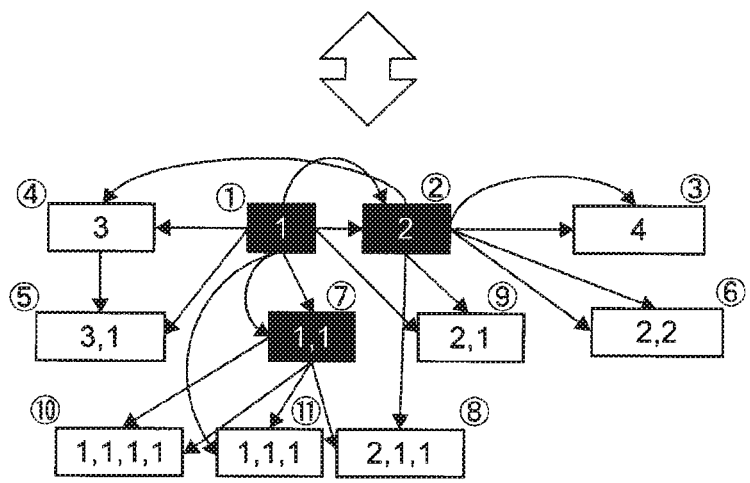
FIG. 9 It depicts an explanatory diagram illustrating an exemplary enumeration plan.

FIG. 9 depicts an explanatory diagram of an exemplary enumeration plan. The table and DAG illustrated in FIG. 9 as an example correspond to each other. The DNF labels that are put with "TRUE" in the cacheFlag in the table, and the black nodes in the DAG are identified as the DNF labels to be cached.

As described above, in the present exemplary embodiment, the enumeration plan generation unit 11 divides each logical formula structure into two so as to minimize the difference between the numbers of features included in the two partial logical formula structures generated from the logical formula structure. In other words, when the enumeration plan generation unit 11 creates a parent-child relationship between the nodes, the enumeration plan generation unit 11 evenly divides each logical formula structure (DNF structure). This can reduce the memory cost.

For example, when a DNF having the length 4 exists, the enumeration plan generation unit 11 does not divide the DNF into a DNF having the length 3 and a DNF having the length 1, but divides the DNF into two DNFs having the length 2. When the DNF is divided into a DNF having the length 3 and a DNF having the length 1, the size of the DNF having the length 3 to be stored in the memory is on the order of the cube. On the other hand, the size of the DNF having the length 2 to be stored in the memory is only on the order of the square.

The DNF search unit 12 generates a new feature by combining the features corresponding to the DNF labels identified by the enumeration plan generation unit 11 in the order of the DNF labels. When the DNF label of which feature is to be generated is identified as the DNF label to be cached by the enumeration plan generation unit 11, the DNF search unit 12 registers the generated feature in the intermediate data storage unit 13. The DNF search unit 12 initially registers the first node (in other words, the original node) in the intermediate data storage unit 13.

Specifically, when the feature generated for a parent DNF label is cached in the intermediate data storage unit 13, the DNF search unit 12 generates a new feature using the feature. In the present exemplary embodiment, the enumeration plan generation unit 11 selects a logical formula structure (DNF label) having high reusability as a logical formula structure to be cached. This selection can reduce the calculation.

Every time the DNF search unit 12 generates a new feature corresponding to each DNF label, the DNF search unit 12 notifies the feature sequential assessment unit 14 of the generated feature.

The intermediate data storage unit 13 stores the new feature generated by the DNF search unit 12. Specifically, the intermediate data storage unit 13 stores each logical formula structure (DNF label) while linking the logical formula structure with the list of the DNFs and vectors. The intermediate data storage unit 13 is implemented, for example, with a magnetic disk.

Figure 10:
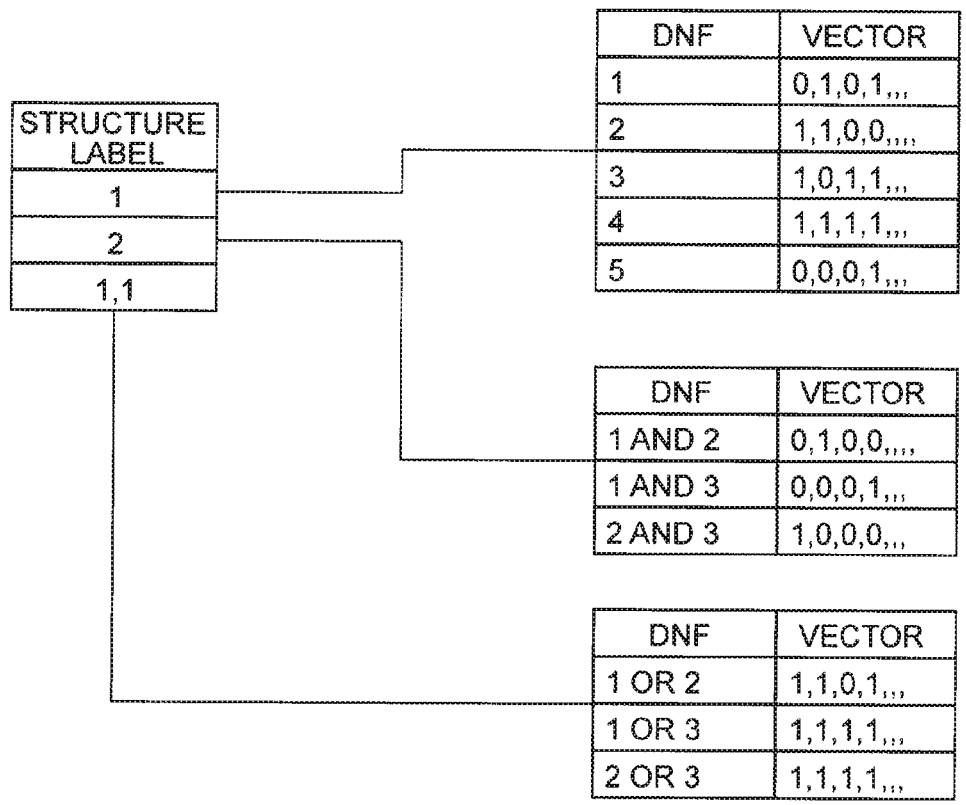
FIG. 10 It depicts an explanatory diagram illustrating exemplary data stored in an intermediate data storage unit 13.

FIG. 10 depicts an explanatory diagram of exemplary data stored in the intermediate data storage unit 13. Each number in the DNF column illustrated in FIG. 10 as an example indicates the type of the feature (the ID number of the feature), the structure label indicates the logical formula structure. The information indicated in the DNF column is for maintaining the permutation of the feature ID numbers, and thus can arbitrarily be encoded. Alternatively, the DNF search unit 12 may arbitrarily compresses the vectors, for example, by substituting the same vectors with different codes, and then store the compressed vectors in the intermediate data storage unit 13.

The feature sequential assessment unit 14 assesses the feature generated by the DNF search unit 12. The feature sequential assessment unit 14 can use the method described in NPL 4 to assess the feature. The method for assessing the feature, however, is not limited to the method described in NPL 4, and the feature sequential assessment unit 14 may use any arbitrary method to assess the feature.

The feature sequential assessment unit 14 of the present exemplary embodiment receives a new feature notified by the DNF search unit 12 one by one every time the DNF search unit 12 generates the new feature, and assesses the received feature. The sequential assessment performed as described above can reduce the cost for storing the features newly generated.

Subsequently, the feature sequential assessment unit 14 stores the assessment result in the output data storage unit 15. The output data storage unit 15 is a storage device that stores the assessment result. The feature sequential assessment unit 14 may select the top (for example, 100) features in accordance with arbitrary scores calculated, for example, by a Hilbert-Schmidt Independence Criterion (HSIC) or a Pearson correlation, and store the selected features in the output data storage unit 15.

In the present exemplary embodiment, the example in which the assessment result is stored in the output data storage unit 15 has been described. The feature sequential assessment unit 14, however, may transmit the assessment result via a communication line to another device (not illustrated).

The enumeration plan generation unit 11, the DNF search unit 12, and the feature sequential assessment unit 14 are implemented with a CPU of a computer that operates in accordance with a program (feature enumeration program). For example, the program is stored in a storage unit (not illustrated) in the feature enumeration system, and the CPU reads the program so as to operate as the enumeration plan generation unit 11, the DNF search unit 12, and the feature sequential assessment unit 14 in accordance with the read program.

Alternatively, the enumeration plan generation unit 11, the DNF search unit 12, and the feature sequential assessment unit 14 may be implemented with dedicated hardware for each unit. Specifically, the feature enumeration system of the present exemplary embodiment may be implemented by the wired or wireless connection between two or more devices physically separate from each other, or by a device.

As described above, in the present exemplary embodiment, the enumeration plan generation unit 11 generates a set of DNF labels each representing a way of combining logical formula expressions each representing a combination of features by use of the features of learning data items and the MaxLen. Furthermore, the enumeration plan generation unit 11 generates partial DNF label by dividing a logical formula expression included in each generated DNF label into two, and then generates an enumeration plan in which the partial DNF labels are linked to the DNF label from which the two partial DNF labels are divided. Subsequently, the DNF search unit 12 generates a new feature that is a combination of the features corresponding to the generated partial DNF labels. At that time, the enumeration plan generation unit 11 divides the DNF label into two such that the numbers of features included in the two partial DNF labels generated from each DNF label are substantially equal.

Using the DNF labels divided described above can achieve rapid enumeration of a new feature while allowing the features to have completeness and reducing the size of the feature created in accordance with the divided DNF label.

Meanwhile, in the present exemplary embodiment, the enumeration plan generation unit 11 generates an enumeration plan representing the relationship between the generated DNF label and the partial DNF labels each representing a part of the generated DNF label as a graph structure. At that time, the enumeration plan generation unit 11 selects the partial DNF labels from the enumeration plan such that the size of a space necessary to store a new feature generated by the DNF search unit 12 can be reduced and more parts of the DNF label can be represented (in other words, the reusability can be increased).

In other words, the relationship that is the components used for generating a new feature (parent-child relationships) are identified as a graph structure for each DNF label, and a subset of nodes is selected in terms of the memory cost for the caching and the calculation cost for the reuse. This can reduce the calculation cost and enumerate the features at high speed, at the same time, reduce waste of the memory for storing the features and exhaustively enumerate a new feature.

In other words, in the present exemplary embodiment, the enumeration plan generation unit 11 automatically determines the method for combining DNFs within the MaxLen, and then generates an enumeration plan while keeping the balance between the size of memory and the amount of calculation. This can enumerate a new feature at high speed while allowing the features to have completeness and reducing waste of memory.

For example, when the enumeration plan illustrated in FIG. 9 as an example is identified, a new feature corresponding to the DNF labels [1], [2], and [1, 1], in other words, the features on the order of the square may be cached. Specifically, when the feature of the DNF label [4] is generated, not the features corresponding to the DNF labels [3], and [1] but the feature corresponding to the DNF label [2] can be used in the present exemplary embodiment. This can reduce waste of the memory and enumerate a new feature at high speed.

Furthermore, DNFs having high reusability are cached in the present exemplary embodiment. This can increase the caching efficiency. For example, when the features of the DNF labels [1, 1, 1, 1], [1, 1, 1], and [2, 1, 1] of the enumeration plan illustrated in FIG. 9 as an example are assessed, it is unnecessary to newly generate a feature corresponding to the DNF label [1, 1].

EXAMPLE

Hereinafter, the present invention will be described with specific examples. The scope of the present invention, however, is not limited to the contents described below. FIGS. 11(a) and 11(b) depict explanatory diagrams of specific examples of the processes in which the DNF search unit 12 creates features and stores the feature to be cached in the intermediate data storage unit 13.

FIG. 11(a) depicts an exemplary process for generating a feature for each DNF label. In the example illustrated in FIG. 11(a), the DNF search unit 12 sequentially generates features from the top row of the table illustrated in FIG. 9. Every time the DNF search unit 12 generates the feature, the DNF search unit 12 outputs the generated feature to the feature sequential assessment unit 14. When the generated feature is a feature to be cached, the DNF search unit 12 stores the generated feature to the intermediate data storage unit 13.

FIG. 11(b) depicts an exemplary process for outputting a combination of the features. In the example illustrated in FIG. 11(b), when a feature corresponding to a DNF label is stored (cached) in the intermediate data storage unit 13, the DNF search unit 12 outputs the feature. On the other hand, when a feature corresponding to a DNF label is not stored (cached) in the intermediate data storage unit 13, the DNF search unit 12 generates a combination of the features. Meanwhile, the DNF search unit 12 generates also a parent DNF.

Furthermore, in the example illustrated in FIG. 11(b), when the labels contain only AND terms, the DNF search unit 12 generates an AND combination. When the terms contained in the labels are not only And terms, the DNF search unit 12 generates an OR combination.

Figure 12:
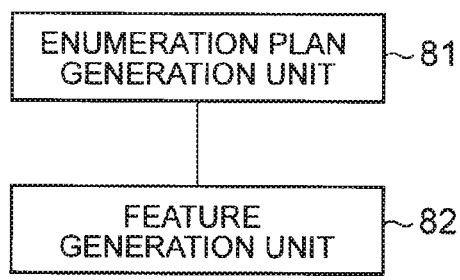
FIG. 12 It depicts a block diagram illustrating the outline of the feature enumeration system according to the present invention.

Next, the outline of the present invention will be described. FIG. 12 depicts a block diagram illustrating the outline of the feature enumeration system according to the present invention. The feature enumeration system according to the present invention includes an enumeration plan generation unit 81 (for example, the enumeration plan generation unit 11) and a feature generation unit 82 (for example, the DNF search unit 12). The enumeration plan generation unit 81 generates a set of logical formula structures (for example, DNF labels) each representing a way of combining the logical formula expressions (for example, DNFs or CNFs) each representing a combination of features by use of the features of learning data items (for example, the two-valued matrix X) and the maximum number of features to be combined (for example, MaxLen), and generates partial logical formula structures (for example, the partial DNF labels) by dividing the logical formula expression included in each generated logical formula structure into two, and generates an enumeration plan (for example, the enumeration plan represented as the tabular form or graph structure illustrated in FIG. 9 as an example) in which the partial logical formula structures are linked to the logical formula structure from which the partial logical formula structures are divided. The feature generation unit 82 generates a new feature that is a combination of the features corresponding to the partial logical formula structures.

The enumeration plan generation unit 81 divides the logical formula structure into two such that the numbers of the features included in the two partial logical formula structures generated from each logical formula structure are substantially equal (for example, the difference between the numbers is minimized).

The units described above can enumerate a new feature at high speed while allowing the features to have completeness and reducing waste of the memory.

Furthermore, the enumeration plan generation unit 81 may generate an enumeration plan in which the relationship between the logical formula structure and the generated partial logical formula structures each representing a part of the logical formula structure is represented as a graph structure (for example, a DAG), and select the partial logical formula structures (for example, having high reusability) from the enumeration plan such that the size of a space necessary to store a new feature generated by the feature generation unit 82 (for example, the memory cost) can be reduced and more parts of the logical formula structure can be represented.

Furthermore, the feature generation unit 82 may store a new feature generated in accordance with the partial logical formula structures selected by the enumeration plan generation unit 81 in a storage device (for example, the intermediate data storage unit 13), and generate a new feature corresponding to other logical formula structures based on the features stored in the storage device.

The new feature stored in the storage device as described above is generated based on the logical formula structure appropriately divided into two. This generation can reduce the size of space and thus can reduce waste of the memory. Furthermore, the logical formula structures selected described above has higher reusability. This can achieve enumeration of a new feature at high speed.

Furthermore, the feature enumeration system may include a feature assessment unit (for example, the feature sequential assessment unit 14) that assesses the feature generated by the feature generation unit 82. At that time, every time the feature generation unit 82 generates a new feature corresponding to the partial logical formula structures, the feature generation unit 82 may transmit the generated feature to the feature assessment unit.

This can reduce the memory space for storing the new feature to be assessed, and thus can increase the memory efficiency.

Furthermore, the enumeration plan generation unit 81 may use Disjunctive normal form (DNF) or Conjunctive normal form (CNF) as the logical formula expression representing a combination of the features. An arbitrary logical formula can be converted into the Disjunctive normal form and Conjunctive normal form with equivalent conversion, and thus can allow the features to have high completeness.

Figure 13:
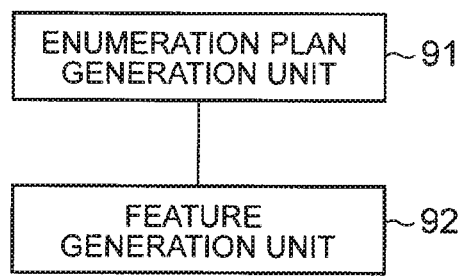
FIG. 13 It depicts a block diagram illustrating another outline of the feature enumeration system according to the present invention.

FIG. 13 depicts a block diagram illustrating another outline of the feature enumeration system according to the present invention. The feature enumeration system according to the present invention includes an enumeration plan generation unit 91 (for example, the enumeration plan generation unit 11) and a feature generation unit 92 (for example, the DNF search unit 12). The enumeration plan generation unit 91 generates a set of logical formula structures (for example, DNF labels) each representing a way of combining logical formula expressions (for example, DNFs or CNFs) each representing a combination of features by use of the features of learning data items (for example, the two-valued matrix X) and the maximum number of features to be combined (for example, MaxLen), and generates an enumeration plan in which the relationship between the logical formula structure and the generated partial logical formula structures (for example, the partial DNF labels) each representing a part of the logical formula structure is represented as a graph structure (for example, a DAG). The feature generation unit 92 generates a new feature that is a combination of the features corresponding to the partial logical formula structures.

The enumeration plan generation unit 91 selects the partial logical formula structures (for example, having high reusability) from the enumeration plan such that the size of a space necessary to store the new feature generated by the feature generation unit 92 (for example, the memory cost) can be reduced and more parts of the logical formula structure can be represented.

The units described above can also enumerate a new feature at high speed while allowing the feature to have high completeness and reducing waste of the memory.

Furthermore, the feature generation unit 92 may store a new feature generated corresponding to the partial logical formula structures selected by the enumeration plan generation unit 91 in a storage device (for example, the intermediate data storage unit 13), and generate a new feature corresponding to other logical formula structures based on the features stored in the storage device.

The present invention has been described above with reference to the exemplary embodiment and the examples. The present invention, however, is not limited to the exemplary embodiment and the examples. The configuration and details of the present invention can variously be changed in the scope of the present invention as is understood by those skilled in the art.

This application claims priority based on Japanese Patent Application No. 2014-114923, filed on Jun. 3, 2014, the discloser of which is hereby incorporated in its entirety.

REFERENCE SIGNS LIST

11 Enumeration plan generation unit
12 DNF search unit
13 Intermediate data storage unit
14 Feature sequential assessment unit
15 Output data storage unit

The invention claimed is:

1. A feature enumeration system comprising:
hardware including a processor;
an enumeration plan generation unit implemented at least by the hardware and that generates a set of logical formula structures each logical formula structure representing a way of combining logical formula expressions each logical formula expression representing a combination of features by use of features of learning data items and a maximum number of features to be combined, generates partial logical formula structures by dividing the logical formula expression included in each of the generated logical formula structure into two, and generates an enumeration plan in which the partial logical formula structures are linked to the logical formula structure from which the partial logical formula structures are divided; and
a feature generation unit implemented at least by the hardware and that generates a new feature that is a combination of features corresponding to the generated partial logical formula structures,
wherein the enumeration plan generation unit divides the logical formula structure into two such that numbers of the features included in the two partial logical formula structures generated from each of the logical formula structure are substantially equal, and
wherein the enumeration plan generation unit sorts the logical formula structure referenced as a parent once or more in descending order and identifies a number of top logical formula structures as logical formula structures to be cached and the identified number of top logical formula structures are equal to or smaller than the cache size.

2. The feature enumeration system according to claim 1, wherein the enumeration plan generation unit generates the enumeration plan in which a relationship between the logical formula structure from the set of logical formula structures and the generated partial logical formula structures each representing a part of the logical formula structure is represented as a graph structure, and selects the partial logical formula structures from the enumeration plan such that a size of a space necessary to store the new feature generated by the feature generation unit is able to be reduced and more parts of the logical formula structure are able to be represented.

3. The feature enumeration system according to claim 2, wherein the feature generation unit stores a new feature generated in accordance with the partial logical formula structures selected by the enumeration plan generation unit in a storage device, and generates a new feature corresponding to other logical formula structures not selected by the enumeration plan generation unit based on the features stored in the storage device.

4. The feature enumeration system according to claim 1, further comprising:
a feature assessment unit implemented at least by the hardware and that assesses the feature generated by the feature generation unit,
wherein, every time the feature generation unit generates the new feature corresponding to each of the partial logical formula structures, the feature generation unit transmits the generated new feature to the feature assessment unit.

5. The feature enumeration system according to claim 1, wherein
the enumeration plan generation unit uses a Disjunctive normal form or a Conjunctive normal form as the logical formula expression representing the combination of the features.

6. The feature enumeration system according to claim 1, wherein
a number of logical formula structures selected by the enumeration plan generation unit is equal to or smaller than the number of logical formula structures that can be stored in the cache size to which a memory size for the generated features is designated.

7. A feature enumeration system comprising:
hardware including a processor;
an enumeration plan generation unit implemented at least by the hardware and that generates a set of logical formula structures each logical formula structure representing a way of combining logical formula expressions each logical formula expression representing a combination of features by use of features of learning data items and a maximum number of features to be combined, and generates an enumeration plan in which a relationship between the generated logical formula structure and partial logical formula structures each partial logical formula structure representing a part of the logical formula structure is represented as a graph structure; and
a feature generation unit implemented at least by the hardware and that generates a new feature that is a combination of features corresponding to the partial logical formula structures, wherein the enumeration plan generation unit selects the partial logical formula structures from the enumeration plan such that a size of a space necessary to store the new feature generated by the feature generation unit is able to be reduced and more parts of the logical formula structure are able to be represented,
wherein the enumeration plan generation unit divides the logical formula structure into two partial logical formula structures such that numbers of the features included in the two partial logical formula structures generated from each of the logical formula structure are substantially equal, and
wherein the enumeration plan generation unit sorts the logical formula structure referenced as a parent once or more in descending order and identifies a number of top logical formula structures as the logical formula structures to be cached and the identified number of top logical formula structures are equal to or smaller than the cache size.

8. The feature enumeration system according to claim 7, wherein the feature generation unit stores a new feature generated in accordance with the partial logical formula structures selected by the enumeration plan generation unit in a storage device, and generates a new feature corresponding to other logical formula structures not selected by the enumeration plan generation unit based on the features stored in the storage device.

9. A feature enumeration method comprising:
generating a set of logical formula structures each logical formula structure representing a way of combining logical formula expressions each logical formula expression representing a combination of features by use of features of learning data items and a maximum number of features to be combined;

generating partial logical formula structures by dividing the logical formula expression included in each of the generated logical formula structure into two, and generating an enumeration plan in which the partial logical formula structures are linked to the logical formula structure from which the partial logical formula structures are divided; and generating a new feature that is a combination of features corresponding to the generated partial logical formula structures, wherein, when the enumeration plan is generated, the logical formula structure is divided into two such that numbers of the features included in the two partial logical formula structures generated from each of the logical formula structure are substantially equal, and the logical formula structure referenced as a parent is sorted once or more in descending order and a number of top logical formula structures are identified as the logical formula structures to be cached and the identified number of top logical formula structures are equal to or smaller than the cache size.

10. The feature enumeration method according to claim 9, further comprising:

generating the enumeration plan in which a relationship between the logical formula structure from the set of logical formula structures and the generated partial logical formula structures each representing a part of the logical formula structure is represented as a graph structure; and selecting the partial logical formula structures from the enumeration plan such that a size of a space necessary to store the generated new feature is able to be reduced and more parts of the logical formula structure are able to be represented.

11. A feature enumeration method comprising:

generating a set of logical formula structures each logical formula structure representing a way of combining logical formula expressions each logical formula expression representing a combination of features by use of features of learning data items and a maximum number of features to be combined;

generating an enumeration plan in which a relationship between the logical formula structure and partial logical formula structures each partial logical formula structure representing a part of the logical formula structure is represented as a graph structure;

selecting the partial logical formula structures from the enumeration plan such that a size of a space necessary to store a new feature generated in accordance with the partial logical formula structures is able to be reduced and more parts of the logical formula structure are able to be represented;

generating the new feature that is a combination of features corresponding to the partial logical formula structures;

sorting the logical formula structure referenced as a parent once or more in descending order;

dividing the logical formula structures into two partial logical formula structures such that numbers of the features included in the two partial logical formula structures generated from each of the logical formula structure are substantially equal; and identifying a number of top logical formula structures as the logical formula structures to be cached and the identified number of top logical formula structures are equal to or smaller than the cache size.

12. The feature enumeration method according to claim 11, further comprising:

storing a new feature generated in accordance with the selected partial logical formula structures in a storage device and generating a new feature corresponding to not selected other logical formula structures based on the features stored in the storage device.

13. A non-transitory computer readable information recording medium storing a feature enumeration program, when executed by a processor, that performs a method for:

generating a set of logical formula structures each logical formula structure representing a way of combining logical formula expressions each logical formula expression representing a combination of features by use of features of learning data items and a maximum number of features to be combined, and generating partial logical formula structures by dividing the logical formula expression included in each of the generated logical formula structure into two and linking the partial logical formula structures to the logical formula structure from which the partial logical formula structures are divided, to generate an enumeration plan; and generating a new feature that is a combination of features corresponding to the generated partial logical formula structures, wherein the logical formula structure is divided into two such that numbers of the features included in the two partial logical formula structures generated from each of the logical formula structure are substantially equal, and the logical formula structure referenced as a parent is sorted once or more in descending order and a number of top logical formula structures are identified as logical formula structures to be cached and the identified number of top logical formula structures are equal to or smaller than the cache size.

14. The non-transitory computer-readable information recording medium according to claim 13, generating an the enumeration plan in which a relationship between the logical formula structure from the set of logical formula structures and the generated partial logical formula structures each representing a part of the logical formula structure is represented as a graph structure, and selecting the partial logical formula structures from the enumeration plan such that a size of a space necessary to store the new generated feature-is able to be reduced and more parts of the logical formula structure are able to be represented.

15. A non-transitory computer readable information recording medium storing a feature enumeration program, when executed by a processor, that performs a method for:

generating a set of logical formula structures each logical formula structure representing a way of combining logical formula expressions each logical formula expression representing a combination of features by use of features of learning data items and a maximum number of features to be combined, and generating an enumeration plan in which a relationship between the logical formula structure and partial logical formula structures each partial logical formula structure representing a part of the logical formula structure is represented as a graph structure;

generating a new feature that is a combination of features corresponding to the partial logical formula structures; and dividing the logical formula structures into two partial logical formula structures such that numbers of the features included in the two partial logical formula structures generated from each of the logical formula structure are substantially equal, wherein the partial logical formula structures are selected from the enumeration plan such that a size of a space necessary to store the new generated feature is able to be reduced and more parts of the logical formula structure are able to be represented, and the logical formula structure referenced as a parent is sorted once or more in descending order and a number of top logical formula structures are identified as logical formula structures to be cached and the identified number of top logical formula structures are equal to or smaller than the cache size.

16. The non-transitory computer-readable information recording medium according to claim 15, storing a new feature generated in accordance with the selected partial logical formula structures in a storage device and generating a new feature corresponding to not selected other logical formula structures based on the features stored in the storage device.

* * * * *